United States Patent [19]

Otsuki et al.

[11] 3,944,565

[45] Mar. 16, 1976

[54] PROCESS FOR PREPARING ALKALI METAL SALTS OF CARBAZOLE

[75] Inventors: Hiroshi Otsuki, Tokyo; Kenzo Sakuma, Fujisawa; Isamu Matsuzawa, Tokyo, all of Japan

[73] Assignee: Takasago Perfumery Co., Ltd., Tokyo, Japan

[22] Filed: Oct. 26, 1973

[21] Appl. No.: 410,151

[30] Foreign Application Priority Data
Oct. 30, 1972 Japan.............................. 47-107940

[52] U.S. Cl.................................. 260/315; 96/1 R
[51] Int. Cl.²........................................ C07D 209/86
[58] Field of Search...................................... 260/315

[56] References Cited
UNITED STATES PATENTS

| | | | |
|---|---|---|---|
| 1,494,879 | 5/1924 | Atack | 260/315 |
| 1,685,624 | 9/1928 | Andrews | 260/315 |
| 2,153,993 | 4/1939 | Reppe et al. | 260/315 |

OTHER PUBLICATIONS

JACS, 71:1028–1030, (1949), Wright.

*Primary Examiner*—Sherman D. Winters
*Attorney, Agent, or Firm*—Sughrue, Rothwell, Mion, Zinn & Macpeak

[57] ABSTRACT

Alkali metal salts of carbazole are prepared by heating carbazole and alkali metal hydroxides with stirring in an organic solvent which forms an azeotrope with water, and removing the resulting water as an azeotrope from the reaction system.

The resulting alkali metal salts of carbazole are useful as a material for the preparation of vinyl carbazole for use in electrophotography. The reaction is promoted particularly by the presence of a small amount of water in the reaction system prior to heating.

8 Claims, No Drawings

PROCESS FOR PREPARING ALKALI METAL SALTS OF CARBAZOLE

BACKGROUND OF THE INVENTION

1. Field of the Invention

This invention relates to process for preparing alkali metal salts of carbazole having high purity.

2. Description of the Prior Art

The alkali metal salts of carbazole are important as intermediates for the preparation of vinyl carbazole. Known methods for preparing the alkali metal salts of carbazole include, for example, a method which involves subjecting carbazole to an alkali fusion (Japanese Pat. No. 170,858), or a method wherein carbazole is reacted with metallic sodium in the presence of gasseous ammonia at an elevated temperature and an elevated pressure (Japanese Pat. No. 169,946). These conventional methods, however, suffer from the disadvantage that not only are there difficulties in the alkali fusion or the use of a high pressure reaction, but also the alkali salt of carbazole produced has a black brown color and is poor in purity to an extent that it is unsuitable as a starting material to prepare vinyl carbazole to be used in preparing modern day electrophotographic materials.

It is an object of this invention to provide a process for preparing alkali metal salts of carbazole, which can be operated safely and easily industrially. Another object of this invention is to provide a process for preparing alkali metal salts of carbazole useful for producing vinyl carbazole of high purity suitable for use in electrophotography.

SUMMARY OF THE INVENTION

Our investigations were conducted with the expectation that a feasible rate of reaction would be obtainable even with a nonhomogeneous reaction if the carbazole and an alkali metal hydroxide were heated with stirring in an organic solvent, such as toluene or xylene, which forms an azeotrope together with water, the effluent steam is cooled and condensed, and the resulting water in a small amount is removed thereby promoting the process of the reaction to the product side. As a result, it was found that greenish yellow carbazole alkali metal salts can be prepared by heating carbazole and an alkali metal hydroxide with stirring in an organic solvent which forms an azeotrope together with water, such as xylene or toluene, separating the water from the resulting azeotrope, and recycling only the solvent to the reaction system thereby to remove the resulting water from the reaction system.

The carbazole alkali metal salts obtained by this method have a high purity. Such purity can not be obtained by a purification of the black brown carbazole alkali metal salts obtained in the conventional methods unless they are decolorized and recrystallized about 10 times. It has also been found that the vinyl carbazole obtained from this carbazole alkali metal salt has markedly superior properties for use in electrophotography as compared with the vinyl carbazole obtained by other methods.

We have additionally found that the rate of reaction of this invention can be accelerated by making the above described nonhomogeneous reaction more homogeneous. Consequently, we have found that when a small amount of water is added to the reaction system prior to the heating step employed in the above described reaction and then an alkali metal hydroxide is reacted with carbazole in this wet condition, the alkali metal hydroxide is well dispersed at the time of heating and reacts very smoothly with the carbazole. The reaction proceeds at a rate which is more than about 5 times faster than the rate of reaction in the absence of water prior to heating. The acceleration of the reaction rate in this manner was quite unexpected since carbazole alkali metal salts are decomposed with water. According to the present invention, there is provided a process for preparing an alkali metal salt of carbazole, which comprises heating carbazole and an alkali metal hydroxide with stirring in an organic solvent which forms an azeotrope with water, and removing the formed water as an azeotrope from the reaction system.

According to another aspect of this invention, there is provided a process for preparing an alkali metal salt of carbazole, which comprises heating carbazole and an alkali metal hydroxide in the presence of a small amount of water with stirring in an organic solvent which forms an azeotrope with water, and removing the resulting water as an azeotrope from the reaction system.

DETAILED DESCRIPTION OF THE INVENTION

Suitable organic solvents forming an azeotrope with water having a boiling point above 100°C which can be used in the present invention are aromatic hydrocarbons such as toluene and xylene, and halogenated hydrocarbons such as tetrachloroethylene.

Of the above described materials, xylene is especially preferred. The amount of the organic solvent or reaction medium is not particularly limited so long as it can maintain the reaction system flowable during stirring. Usually, a suitable amount of the organic solvent is about 3.5 to 5 times, preferably 4 times, by weight to the total amount by weight of the carbazole and the alkali metal hydroxide. Examples of suitable alkali metal hydroxides are sodium hydroxide and potassium hydroxide, the latter being especially preferred. Preferably, the alkali metal hydroxide is used in a finely divided form, e.g., a powder form. An appropriate amount of the alkali metal hydroxide is about an equimolar amount, e.g., a molar ratio of 1:1 to 1:1.1 preferably 1:1.1 based on the amount of carbazole. When water is to be added to the reaction system for promoting the reaction, it is preferably added before heating. The amount of water generally used is about 0.3 to 0.35 mole, preferably 0.33 mol, per mole of the alkali metal hydroxide.

The reaction is generally performed at the boiling point of the organic solvent used, for example, at a temperature of 100° to 120°C. Preferred results are obtained with preferably a temperature of at least 100°C. In performing the reaction, the azeotrope should be collected outside the reaction system so that it can not return directly to the reaction system.

In this way only the upper organic solvent layer is recycled to the reaction system to allow the reaction to proceed automatically. The reaction ends when the amount of effluent water reaches the theoretical calculated amount. The reaction time is, for example, about 2.5 to 4 hours, more generally about 3 hours in xylene, when the reaction is performed and water is added beforehand to promote the reaction, and about 13 to 17 hours, more generally 15 hours when water is not added beforehand.

Thus, the alkali metal salts of carbazole are formed.

For producing vinyl carbazole, the reaction mixture so obtained is directly subjected to an ethylolation reaction.

In order to obtain the carbazole alkali metal salts as crystals, the reaction mixture is cooled, and the resulting crystals are separated from the organic solvent by filtration, followed by drying the crystals, thereby to form high purity carbazole alkali metal salt crystals. If desired, the crystals can be recrystallized from tetrahydrofuran to obtain a purer product.

Synthesis of N-vinyl carbazole from the alkali metal carbazole salt is known in the art, for example, as described in German Pat. No. 618,120, British Pat. No. 641,437 and U.S. Pat. Nos. 3,037,861 and 3,232,755. The following Examples illustrate the invention more specifically. Unless otherwise indicated, all parts and percents are by weight.

EXAMPLE 1

A 2-liter four-necked flask equipped with a thermometer, a water receiver and a stirrer was charged with 167 g (1 mol) of carbazole and 56 g (1 mol) of powdered potassium hydroxide and 700 ml. of xylene was added. The mixture was boiled by heating with stirring. The vaporous azeotropic mixture obtained was condensed, and the water was separated and led to the water receiver. Over a period of about 15 hours, 18 ml. of water was recovered, and the reaction was stopped. The carbazole potassium salt despersed in xylene was separated by filtration and dried to afford 190 g (yield 93%) of the carbazole potassium salt as light yellow crystals.

EXAMPLE 2

The procedure of Example 1 was repeated except that 6 ml. of water was added to the materials charged. The reaction was completed in about 3 hours with a recovery of 24 ml. of water.

The reaction mixture was treated in the same way as described in Example 1 to afford 200 g (yield 98%) of carbazole potassium salt.

While the invention has been described in detail and with reference to specific embodiments thereof, it will be apparent to one skilled in the art that various changes and modifications can be made therein without departing from the spirit and scope thereof.

What is claimed is:

1. A process for preparing an alkali metal salt of carbazole, which comprises heating
    a. carbazole,
    b. an alkali metal hydroxide, and
    c. water, wherein the molar ratio of water to said alkali metal hydroxide is about 0.3:1 to 0.35:1 and wherein said water is added to the reaction system prior to said heating, with stirring in
    d. an organic solvent which forms an azeotrope with water, and removing the water formed in the reaction as an azeotrope from the reaction system.

2. The process of claim 1, wherein said alkali metal hydroxide is sodium hydroxide or potassium hydroxide.

3. The process of claim 2, wherein said alkali metal hydroxide is potassium hydroxide.

4. The process of claim 1, wherein said alkali metal hydroxide and said carbazole are present in about equimolar amounts.

5. The process of claim 1, wherein said organic solvent is an aromatic hydrocarbon solvent, a halogenated hydrocarbon solvent or a mixture thereof.

6. The process of claim 5, wherein said organic solvent is toluene or xylene.

7. The process of claim 1, wherein the weight ratio of the weight of said organic solvent to the combined weight of said carbazole and said alkali metal hydroxide is about 3.5 : 1 to 5 : 1.

8. The process of claim 1, wherein said heating is at a temperature of at least 100°C.

* * * * *